US008536278B2

(12) United States Patent
Funk et al.

(10) Patent No.: US 8,536,278 B2
(45) Date of Patent: Sep. 17, 2013

(54) METHOD FOR THE SURFACE POST-CROSSLINKING OF WATER ABSORBING POLYMER PARTICLES

(75) Inventors: Rüdiger Funk, Niedernhausen (DE); Wilfried Heide, Freinsheim (DE); Uwe Stueven, Bad Soden (DE)

(73) Assignee: BASF SE, Ludwigshafen (DE)

( * ) Notice: Subject to any disclaimer, the term of this patent is extended or adjusted under 35 U.S.C. 154(b) by 241 days.

(21) Appl. No.: 13/002,855

(22) PCT Filed: Jul. 10, 2009

(86) PCT No.: PCT/EP2009/058798
§ 371 (c)(1),
(2), (4) Date: Jan. 6, 2011

(87) PCT Pub. No.: WO2010/004020
PCT Pub. Date: Jan. 14, 2010

(65) Prior Publication Data
US 2011/0118419 A1 May 19, 2011

(30) Foreign Application Priority Data
Jul. 11, 2008 (EP) .................................... 08160175

(51) Int. Cl.
*C08F 8/00* (2006.01)
(52) U.S. Cl.
USPC ........... 525/303; 525/286; 525/301; 502/402; 502/404; 252/194
(58) Field of Classification Search
USPC ................. 525/286, 303, 301; 502/402, 404; 252/194
See application file for complete search history.

(56) References Cited

U.S. PATENT DOCUMENTS

| 5,462,972 | A | 10/1995 | Smith et al. |
| 6,350,710 | B1 | 2/2002 | Jonas et al. |
| 2002/0034562 | A1* | 3/2002 | Sundram et al. ................. 426/2 |
| 2005/0053681 | A1* | 3/2005 | Gormley et al. .............. 424/769 |
| 2005/0080194 | A1* | 4/2005 | Satake et al. .................. 525/195 |
| 2008/0200583 | A1 | 8/2008 | Herth et al. |
| 2008/0221229 | A1 | 9/2008 | Torii et al. |

FOREIGN PATENT DOCUMENTS

| DE | 10130021 A1 | 1/2003 |
| DE | 102005004285 A1 | 8/2006 |
| EP | 668 080 A2 | 8/1995 |
| EP | 0 780 424 A1 | 6/1997 |
| JP | 09272806 A * | 10/1997 |
| WO | WO-9118042 A1 | 11/1991 |
| WO | WO-2004069404 A1 | 8/2004 |
| WO | WO-2004069936 A1 | 8/2004 |
| WO | WO-2005092955 A1 | 10/2005 |
| WO | WO-2009005114 A1 | 1/2009 |
| WO | WO 2009041731 A1 * | 4/2009 |

OTHER PUBLICATIONS

Graham, Andrew T., et al. *Modern Superabsorbent Polymer Technology*, "Solution Polymerization: Unit Operations and Their Effect on Product Quality." New York: John Wiley & Sons, Inc., 1998, pp. 71-103.
Frank, *Ullmann's Encyclopedia of Industrial Chemistry*, 6th Edition, vol. 35, pp. 73-93, Wiley-VCH (2003).
International Search Report in International Application No. PCT/EP2009/058798, dated Sep. 24, 2009.

* cited by examiner

*Primary Examiner* — Mark Kaucher
(74) *Attorney, Agent, or Firm* — Marshall, Gerstein & Borun LLP

(57) ABSTRACT

A process for producing water-absorbing polymer particles, wherein the water-absorbing polymer particles are surface postcrosslinked with unsaturated fatty acids or derivatives thereof.

17 Claims, No Drawings

METHOD FOR THE SURFACE POST-CROSSLINKING OF WATER ABSORBING POLYMER PARTICLES

CROSS-REFERENCE TO RELATED APPLICATIONS

This is the U.S. national phase of International Application No. PCT/EP2009/058798, filed Jul. 10, 2009, which claims the benefit of European patent Application No. 08160175.9, filed Jul. 11, 2008.

The present invention relates to a process for producing water-absorbing polymer particles, wherein the water-absorbing polymer particles are surface postcrosslinked with unsaturated fatty acids or derivatives thereof.

Water-absorbing polymers are used to produce diapers, tampons, sanitary napkins and other hygiene articles, but also as water-retaining agents in market gardening. The water-absorbing polymer particles are also referred to as superabsorbents and consist of hydrophilic polymers which are so highly crosslinked that they are no longer soluble.

The preparation of the water-absorbing polymers is described, for example, in the monograph "Modern Superabsorbent Polymer Technology", F. L. Buchholz and A. T. Graham, Wiley-VCH, 1998, pages 71 to 103, and in Ullmann's Encyclopedia of Industrial Chemistry, 6th edition, volume 35, pages 73 to 93.

The properties of the water-absorbing polymer particles can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the performance properties in the diaper, such as permeability of the swollen gel bed (SFC) and absorption under a pressure of 49.2 g/cm$^2$ (AUL0.7 psi) or more, water-absorbing polymer particles are typically surface postcrosslinked. This increases only the degree of crosslinking of the particle surface, which allows the centrifuge retention capacity (CRC) and the absorption under a pressure of 49.2 g/cm$^2$ (AUL0.7 psi) to be at least partially decoupled. For the surface postcrosslinking, dried, ground and screened water-absorbing polymer particles (base polymer) are preferably coated with a surface postcrosslinker and thermally surface postcrosslinked.

In the case of use of di- and polyfunctional epoxides, it is possible to conduct thermal surface postcrosslinking at particularly low temperatures. For instance, for surface postcrosslinking with ethylene glycol diglycidyl ether, even 30 minutes at 140° C. are sufficient. EP 0 668 080 A2 and 0 780 424 A1 describe processes for increasing the conversion of the epoxides used, since residual amounts of the epoxides used for surface postcrosslinking which remain in the end product are said to be toxicologically unsafe.

It was an object of the present invention to provide a process for thermally surface postcrosslinking water-absorbing polymer particles, wherein the thermal surface postcrosslinking is performed at low temperatures and the use of toxicologically unsafe surface postcrosslinkers can nevertheless be dispensed with.

The object is achieved by a process for producing surface postcrosslinking water-absorbing polymer particles which are obtained by polymerizing a monomer solution or suspension comprising
a) at least one ethylenically unsaturated monomer which bears acid groups and may be at least partially neutralized,
b) at least one crosslinker,
c) at least one initiator,
d) optionally one or more ethylenically unsaturated monomers copolymerizable with the monomers mentioned under a) and
e) optionally one or more water-soluble polymers,
at least one surface postcrosslinker is applied to the water-absorbing polymer particles and the water-absorbing polymer particles are thermally surface postcrosslinked, wherein the surface postcrosslinker is at least one ethylenically unsaturated carboxylic acid having at least 10 carbon atoms, or a salt, ester and/or epoxidation product thereof.

The ethylenically unsaturated carboxylic acids or salts, esters and/or epoxidation products thereof preferably have at least 12, more preferably at least 14, most preferably at least 16, and typically fewer than 30, carbon atoms.

The ethylenically unsaturated carboxylic acids or salts and/or esters thereof preferably have at least two, more preferably at least three, most preferably at least 4, carbon-carbon double bonds (ethylenically unsaturated groups).

Advantageously, ethylenically unsaturated carboxylic acids with adjacent carbon-carbon double bonds or salts and/or esters thereof are used. Adjacent carbon-carbon double bonds are two carbon-carbon double bonds which are separated by exactly one carbon atom, preferably a methylene group, as, for example, in linoleic acid and linolenic acid. These ethylenically unsaturated carboxylic acids and salts and/or esters thereof are particularly reactive.

In a preferred embodiment of the present invention, the ethylenically unsaturated carboxylic acid or salt and/or ester thereof additionally comprises at least one epoxy group, preferably at least one epoxy group adjacent to the carbon-carbon double bond, as, for example, in vernolic acid.

The ethylenically unsaturated carboxylic acids or salts and/or esters thereof usable in the process according to the invention are preferably obtained from renewable raw materials. Suitable renewable raw materials are vegetable and/or animal oils, such as butterfat, rapeseed oil, castor oil, chicken fat, lemonseed oil, cocoa butter, coconut oil, cod liver oil, corn germ oil, cottonseed oil, porcine fat, linseed oil, herring oil, olive oil, palm oil, palm kernel oil, groundnut oil, grapeseed oil, rice oil, safflower oil, sesame oil, soybean oil, sunflower oil, bovine tallow and tung oil. The ethylenically unsaturated carboxylic acids and salts and/or esters thereof (unsaturated fatty acids) which occur in renewable raw materials are preferred.

The ethylenically unsaturated carboxylic acids and the salts and/or esters thereof can also be used together with other carboxylic acids or salts and/or esters thereof, where the proportion of ethylenically unsaturated carboxylic acid or salt and/or ester thereof in the mixture is preferably at least 30% by weight, more preferably at least 40% by weight, most preferably at least 50% by weight, i.e. the fatty acid mixtures obtained, for example, from animal and/or vegetable oils can, if the proportion of unsaturated fatty acids is high enough, be used directly.

Very particular preference is given to using linseed oil and/or vernonia oil and the fatty acid mixtures obtained from linseed oil and/or vernonia oil. The carboxylic acids present in linseed oil are, for example, stearic acid (from approx. 1 to 4% by weight), palmitic acid (from approx. 4 to 8% by weight), linoleic acid (from approx. 10 to 30% by weight), oleic acid (from approx. 15 to 30% by weight) and linolenic acid (from approx. 40 to 68% by weight).

Esters of the ethylenically unsaturated carboxylic acids are preferably understood to mean fats and oils, i.e. fatty acid esters of glycerol.

When the ethylenically unsaturated carboxylic acids or salts and/or esters thereof are used as surface postcrosslinkers, the surface postcrosslinking is advantageously performed in the presence of oxygen. The partial oxygen pressure during the thermal surface postcrosslinking in the apparatus used is preferably at least 10 mbar, more preferably at least 50 mbar, most preferably at least 100 mbar. The thermal surface post-crosslinking can be carried out, for example, under air. Oxygen reacts with the ethylenically unsaturated carboxylic acids to give hydroperoxides which lead to free-radical crosslinking. This crosslinking of unsaturated fatty acids is also referred to as "drying".

The "drying" of the ethylenically unsaturated carboxylic acid enables thermal surface postcrosslinking at significantly lower temperatures, preferably from 50 to 150° C., more preferably from 60 to 130° C., most preferably from 70 to 100° C. However, it will be appreciated that the surface postcrosslinking can also be performed at higher temperatures.

In a very particularly preferred embodiment of the present invention, the carbon-carbon double bonds of the ethylenically unsaturated carboxylic acids are converted before the surface postcrosslinking at least partially to the corresponding epoxy groups. The epoxidation of carbon-carbon double bonds is described, for example, in Organikum—Organisch-chemisches Grundpraktikum, 16th edition, VEB Deutscher Verlag der Wissenschaften, Berlin, 1986, pages 257 to 261.

In a further very particularly preferred embodiment of the present invention, the carbon-carbon double bonds of esters of the ethylenically unsaturated carboxylic acids are converted before the surface postcrosslinking at least partially to the corresponding epoxy groups. Very particular preference is given to using epoxidized vegetable and/or animal oils as surface postcrosslinkers. The preparation of epoxidized vegetable and/or animal oils is described, for example, in J. Polym. Sci. Part A: Polym. Chem. 2006, volume 44, pages 6717 to 6727, and Eur. Polym. J. 2005, volume 41, pages 231 to 237.

When the epoxidation products are used as surface postcrosslinkers, the surface postcrosslinking is advantageously performed in the absence of oxygen. The partial oxygen pressure during the thermal surface postcrosslinking in the apparatus used is therefore preferably less than 100 mbar, more preferably less than 50 mbar, most preferably less than 10 mbar.

The thermal surface postcrosslinking can at significantly lower temperatures, preferably from 50 to 150° C., more preferably from 60 to 130° C., most preferably from 70 to 100° C. It will be appreciated that the surface postcrosslinking can also be performed at higher temperatures.

The preparation of the usually water-insoluble water-absorbing polymer particles will be illustrated in detail hereinafter.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 21.0 g/cm$^2$ (AUL0.3 psi) passes through a maximum.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 95 mol %, more preferably from 30 to 80 mol %, most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably from 0.5 to 15% by weight, more preferably from 1 to 10% by weight, most preferably from 2 to 8% by weight, the residual moisture content being determined by the EDANA (European Disposables and Nonwovens Association) recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm, very particularly from 300 to 500 μm. The mean particle size of the product fraction may be determined by means of the EDANA (European Disposables and Nonwovens Association) recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the permeability (SFC). The proportion of excessively small polymer particles ("fines") should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles after the surface postcrosslinking.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until in an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles are surface postcrosslinked with ethylenically unsaturated carboxylic acids or derivatives thereof.

The amount of ethylenically unsaturated carboxylic acid or derivative thereof is preferably from 0.001 to 2% by weight, more preferably from 0.02 to 1% by weight, most preferably from 0.05 to 0.2% by weight, based in each case on the water-absorbing polymer particles.

The ethylenically unsaturated carboxylic acids and derivatives thereof are preferably used in dilute form, i.e. dissolved or dispersed in a suitable solvent, for example water, methanol, isopropanol, 1,3-propanediol, ethylene glycol, propylene glycol, polyethylene glycol and/or polypropylene glycol. In order to improve the dispersion in water and the wetting behavior of the dispersion, it is also possible instead of the ethylenically unsaturated carboxylic acids to use the salts thereof, for example the sodium salts.

In addition, it is also possible to use further surface postcrosslinkers. Suitable further surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable further surface postcrosslinkers are cyclic carbonates in DE 40 20 780 C1,2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred further surface postcrosslinkers are ethylene carbonate and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The further surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent for the further surface postcrosslinkers, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, from 0.001 to 1.5% by weight, preferably from 0.005 to 1% by weight, more preferably from 0.02 to 0.8% by weight, based in each case on the polymer particles.

The surface postcrosslinking is typically performed in such a way that a solution or dispersion of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution or dispersion of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The thermal drying is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

When, in addition to the inventive surface postcrosslinkers, further surface postcrosslinkers are also used, it may be appropriate, owing to the possibly lower reactivity of these further surface postcrosslinkers, to perform the thermal surface postcrosslinking at higher temperatures, typically at from 100 to 250° C., preferably at from 120 to 220° C., more preferably at from 130 to 210° C., most preferably at from 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or subsequently moistened. Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil®, and surfactants, such as Span® 20.

The water-absorbing polymer particles produced by the process according to the invention have a moisture content of preferably from 0 to 15% by weight, more preferably from 0.2 to 10% by weight, most preferably from 0.5 to 8% by weight, the water content being determined by the EDANA (European Disposables and Nonwovens Association) recommended test method No. WSP 230.2-05 "Moisture Content".

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by the EDANA (European Disposables and Nonwovens Association) recommended test method No. WSP 241.2-05 "Centrifuge Retention Capacity".

The water-absorbing polymer particles produced by the process according to the invention have an absorption under a pressure of 49.2 g/cm$^2$ (AUL0.7 psi) of typically at least 15 g/g, preferably at least 20 g/g, preferentially at least 22 g/g, more preferably at least 24 g/g, most preferably at least 26 g/g. The absorption under a pressure of 49.2 g/cm$^2$ (AUL0.7 psi) of the water-absorbing polymer particles is typically less than 35 g/g. The absorption under a pressure of 49.2 g/cm$^2$ is determined analogously to the EDANA (European Disposables and Nonwovens Association) recommended test method No. WSP 242.2-05 "Absorption under Pressure", except that a pressure of 49.2 g/cm$^2$ (AUL0.7 psi) is established instead of a pressure of 21.0 g/cm$^2$ (AUL0.3 psi).

The present invention further provides water-absorbing polymer particles obtainable by the process according to the invention, and hygiene articles which comprise these water-absorbing polymer particles.

Methods:

The analyses should, unless stated otherwise, be performed at an ambient temperature of 23±2° C. and a relative air humidity of 50±10%. The water-absorbing polymer particles are mixed thoroughly before the analysis.

Centrifuge Retention Capacity

The centrifuge retention capacity (CRC) is determined by the EDANA (European Disposables and Nonwovens Association) recommended test method No. WSP 241.2-05 "Centrifuge Retention Capacity".

Absorption Under a Pressure of 21.0 g/cm$^2$

The absorption under a pressure of 21.0 g/cm$^2$ (AUL0.3 psi) is determined by the EDANA (European Disposables and Nonwovens Association) recommended test method No. WSP 242.2-05 "Absorption under Pressure".

The EDANA test methods are obtainable, for example, from the European Disposables and Nonwovens Association, Avenue Eugene Plasky 157, B-1030 Brussels, Belgium.

EXAMPLES

Example 1

Preparation of the Base Polymer

By continuously mixing the deionized water, 50% by weight sodium hydroxide solution and acrylic acid, an acrylic acid/sodium acrylate solution was prepared, such that the degree of neutralization corresponded to 72 mol %. The solids content of the monomer solution was 40% by weight.

The polyethylenically unsaturated crosslinker used was triply ethoxylated glyceryl triacrylate. The amount used was 1.3 kg of crosslinker per t of monomer solution.

To initiate the free-radical polymerization, 1 kg of a 0.25% by weight aqueous hydrogen peroxide solution, 1.5 kg of a 30% by weight aqueous sodium peroxide disulfate solution and 1 kg of a 1% by weight aqueous ascorbic acid solution were used per t of monomer solution.

The throughput of the monomer solution was 18 t/h. At the feed, the reaction solution had a temperature of 30° C.

The individual components were metered in the following amounts continuously into a List Contikneter continuous leader reactor with a volume of 6.3 m$^3$ (LIST AG, Arisdorf, Switzerland):

18 t/h of monomer solution
23.4 kg/h of polyethylene glycol-400 diacrylate
45 kg/h of hydrogen peroxide solution/sodium peroxodisulfate solution
18 kg/h of ascorbic acid solution Between the addition point for the crosslinker and the addition sites for the initiators, the monomer solution was inertized with nitrogen.

After approx. 50% of the residence time, there was additional metered addition of fines obtained from the production process by grinding and sieving (1000 kg/h) into the reactor. The residence time of the reaction mixture in the reactor was 15 minutes.

The resulting product gel was applied to a belt drier. On the belt drier, an air/gas mixture flowed continuously around the polymer gel, which was dried at 175° C. The residence time in the belt drier was 37 minutes.

The dried polymer gel was ground and sieved to a particle size fraction of 150 to 850 μm. The base polymer thus obtained had a centrifuge retention capacity (CRC) of 36.5 g/g and an absorption under a pressure of 21.0 g/cm$^2$ (AUL0.3 psi) of 12.8 g/g.

Example 2

Comparative Example

The base polymer prepared in Example 1 (200 g) was heat-treated in a vacuum drying cabinet (Heraeus VACUTHERM VT 6060M; Kendro Laboratory Products GmbH, Germany) at 150° C. for 60 minutes.

The heat-treated base polymer had a centrifuge retention capacity (CRC) of 38.8 g/g and an absorption under a pressure of 21.0 g/cm$^2$ (AUL0.3 psi) of 13.9 g/g.

Example 3

The base polymer prepared in Example 1 (200 g) was sprayed in a food processor (ProfiMixx 47; Robert Bosch GmbH; Germany) at stirrer speed 4 by means of a two-substance nozzle (spray pressure 0.2 bar, N$_2$, 8 g/min) with a surface postcrosslinker solution consisting of 1.0 g of linseed oil and 7.0 g of isopropanol. The moist polymer particles were homogenized once again with a spatula and then heat-treated in a vacuum drying cabinet (Heraeus VACUTHERM VT 6060M; Kendro Laboratory Products GmbH, Germany) at 150° C. for 60 minutes.

The postcrosslinked polymer particles were sieved through an 850 μm protective sieve and analyzed.

The surface postcrosslinked base polymer had a centrifuge retention capacity (CRC) of 37.7 g/g and an absorption under a pressure of 21.0 g/cm$^2$ (AUL0.3 psi) of 16.9 g/g.

Example 4

The procedure was as in Example 3, except that a surface postcrosslinker solution consisting of 1.0 g of linseed oil, 6.6 g of isopropanol and 0.4 g of water was used.

The surface postcrosslinked base polymer had a centrifuge retention capacity (CRC) of 38.1 g/g and an absorption under a pressure of 21.0 g/cm$^2$ (AUL0.3 psi) of 22.9 g/g.

The invention claimed is:

1. A process for surface postcrosslinking water-absorbing polymer particles which are obtained by polymerizing a monomer solution or suspension comprising
   a) at least one ethylenically unsaturated monomer bearing an acid group,
   b) at least one crosslinker,
   c) at least one initiator,
   d) optionally one or more ethylenically unsaturated monomer copolymerizable with the monomer mentioned under a), and
   e) optionally one or more water-soluble polymer,
   at least one surface postcrosslinker is applied to the water-absorbing polymer particles and the water-absorbing polymer particles are thermally surface postcrosslinked, wherein the surface postcrosslinker comprises at least one ester of an ethylenically unsaturated carboxylic acid having at least 10 carbon atoms and/or epoxidation product thereof, wherein the ester of the ethylenically unsaturated carboxylic acid is a vegetable oil and/or animal oil, wherein a proportion of the ethylenically unsaturated carboxylic acid is at least 30% by weight based on the total amount of carboxylic acids in the vegetable oil and/or animal oil.

2. The process according to claim 1, wherein the ethylenically unsaturated carboxylic acid ester has at least two carbon-carbon double bonds.

3. The process according to claim 1, wherein the ethylenically unsaturated carboxylic acid ester has at least two adjacent carbon-carbon double bonds.

4. The process according to claim 1, wherein the ethylenically unsaturated carboxylic acid ester, in addition to the carbon-carbon double bond, has at least one epoxy group.

5. The process according to claim 1, wherein the ethylenically unsaturated carboxylic acid ester additionally has at least one epoxy group adjacent to a carbon-carbon double bond.

6. The process according to claim 1, wherein the ethylenically unsaturated carboxylic acid ester comprises a linolenic acid ester and/or a vernolic acid ester thereof.

7. The process according to claim 1, wherein the ethylenically unsaturated carboxylic acid ester is a naturally occurring ethylenically unsaturated carboxylic acid ester, and is used in a mixture with further naturally occurring carboxylic acids or salts or esters thereof, where the proportion of the ethylenically unsaturated carboxylic acid ester in the mixture is at least 30% by weight.

8. The process according to claim 1, wherein the surface postcrosslinker comprises an epoxidation product of the ethylenically unsaturated carboxylic acid ester.

9. The process according to claim 1, wherein the vegetable oil comprises linseed oil and/or vernonia oil.

10. The process according to claim 1, wherein the thermal surface postcrosslinking is performed at from 50 to 150° C. in the presence of oxygen.

11. The process according to claim 1, wherein the surface postcrosslinker comprises an epoxidized vegetable oil and/or animal oil.

12. The process according to claim 1, wherein the water-absorbing polymer particles have a centrifuge retention capacity of at least 15 g/g.

13. Water-absorbing polymer particles obtainable by a process of claim 1.

14. A hygiene article comprising water-absorbing polymer particles according to claim 13.

15. A process for surface postcrosslinking water-absorbing polymer particles which are obtained by polymerizing a monomer solution or suspension comprising
   a) at least one ethylenically unsaturated monomer bearing an acid group,
   b) at least one crosslinker,
   c) at least one initiator,
   d) optionally one or more ethylenically unsaturated monomer copolymerizable with the monomer mentioned under a), and
   e) optionally one or more water-soluble polymer,
   at least one surface postcrosslinker is applied to the water-absorbing polymer particles and the water-absorbing polymer particles are thermally surface postcrosslinked, wherein the surface postcrosslinker comprises at least one epoxidized vegetable oil and/or animal oil, wherein a proportion of epoxidized vegetable oil and/or animal oil is at least 30% by weight based on the total amount of carboxylic acids in the vegetable oil and/or animal oil.

16. The process according to claim 15, wherein the epoxidized vegetable oil comprises epoxidized linseed oil.

17. The process according to claim 15, wherein the vegetable oil is epoxidized linseed oil and/or epoxidized vernonia oil.

* * * * *